(12) United States Patent
Warner et al.

(10) Patent No.: US 9,763,902 B2
(45) Date of Patent: Sep. 19, 2017

(54) METHOD FOR PREPARATION OF N-ACETYL CYSTEINE AMIDE

(71) Applicant: NaCuity Pharmaceuticals, Inc., Fort Worth, TX (US)

(72) Inventors: John C. Warner, Wilmington, MA (US); Srinavasa Cheruku, Wilmington, MA (US); Sambaiah Thota, Wilmington, MA (US); John W. Lee, Wilmington, MA (US)

(73) Assignee: NACUITY PHARMACEUTICALS, INC, Fort Worth, TX (US)

( * ) Notice: Subject to any disclaimer, the term of this patent is extended or adjusted under 35 U.S.C. 154(b) by 0 days.

(21) Appl. No.: 15/300,092

(22) PCT Filed: Mar. 27, 2015

(86) PCT No.: PCT/US2015/022910
§ 371 (c)(1),
(2) Date: Sep. 28, 2016

(87) PCT Pub. No.: WO2015/148880
PCT Pub. Date: Oct. 1, 2015

(65) Prior Publication Data
US 2017/0183302 A1 Jun. 29, 2017

Related U.S. Application Data

(60) Provisional application No. 61/972,133, filed on Mar. 28, 2014.

(51) Int. Cl.
*C07C 311/29* (2006.01)
*C07C 321/00* (2006.01)
*A61K 31/195* (2006.01)
*A61K 38/04* (2006.01)
*A61K 31/095* (2006.01)
*A61K 31/16* (2006.01)
*A61K 31/198* (2006.01)

(52) U.S. Cl.
CPC .......... *A61K 31/195* (2013.01); *A61K 31/095* (2013.01); *A61K 31/16* (2013.01); *A61K 31/198* (2013.01); *A61K 38/04* (2013.01); *C07C 311/29* (2013.01); *C07C 321/00* (2013.01)

(58) Field of Classification Search
None
See application file for complete search history.

(56) References Cited

U.S. PATENT DOCUMENTS 6,420,429 B1  7/2002 Atlas et al.

FOREIGN PATENT DOCUMENTS

WO  2004012652 A2  2/2004

OTHER PUBLICATIONS

Supelco "Methanolic H2SO4 (10°/o v/v)" 1997, Sigma-Aldrich Co., 2 Pages.

*Primary Examiner* — Kristin Vajda
(74) *Attorney, Agent, or Firm* — Edwin S. Flores; Chalker Flores LLP

(57) ABSTRACT

The present application discloses an efficient process for the preparation of N-acetyl-L-cysteine amide (NACA) starting with N-acetyl-L-cysteine.

20 Claims, No Drawings

METHOD FOR PREPARATION OF N-ACETYL CYSTEINE AMIDE

CROSS-REFERENCE TO RELATED APPLICATIONS

This application is U.S. 371 National Phase Application of PCT No. PCT/US2015/022910, international filing date of 27 Mar. 2015, title, METHOD FOR THE PREPARATION OF N-ACETYL CYSTEINE AMIDE, and claims benefit of U.S. Provisional U.S. Ser. No. 61/972,133, filed on 28 Mar. 2014.

STATEMENT OF FEDERALLY FUNDED RESEARCH

None.

BACKGROUND OF THE APPLICATION

Decreased glutathione (GSH) availability in the brain is linked to several neurodegenerative diseases including Parkinson's disease. Means of restoring GSH levels include delivery of GSH precursors, e.g. N-acetyl cysteine, N-acetyl cysteine amide (NACA) or cysteine to the brain. However, directly administered, these GSH precursors have limited therapeutic usefulness because of their limited bioavailability.

The preparation of N-acetyl cysteine amide (NACA) has been previously described in *J. Med. Chem.* 1967, 10, 1172-1176.

There is a need for developing an efficient method for the effective, large scale synthesis of N-acetyl cysteine amide that provides the product in high chemical yields and high chemical and enantiomeric purity.

SUMMARY OF THE APPLICATION

This disclosure describes an efficient method or process for the preparation of NACA in high chemical yields and high enantiomeric purity. Specifically, disclosed herein is a process comprising:
contacting N-acetyl-L-cysteine with an organic alcohol and an inorganic acid to form an organic solution containing N-acetyl-L-cysteine ester;
neutralizing the acid in the organic solution with an aqueous solution containing a base to form a neutralized mixture;
separating an organic solution containing N-acetyl-L-cysteine ester from the neutralized mixture;
removing the N-acetyl-L-cysteine ester from the organic solution under reduced pressure; and
contacting the N-acetyl-L-cysteine ester with ammonia.

In one embodiment, there is provided a process for the preparation of N-acetyl-L-cysteine amide (NACA) comprising:
a) contacting N-acetyl-L-cysteine with an alcohol and an acid under condition sufficient to form an organic solution containing N-acetyl-L-cysteine ester;
b) neutralizing the acid in the organic solution with an aqueous solution containing a base to form a neutralized mixture;
c) separating the organic solution containing N-acetyl-L-cysteine ester from the aqueous solution;
d) removing the organics under reduced pressure to provide the N-acetyl-L-cysteine ester; and e) contacting the N-acetyl-L-cysteine ester with ammonia under conditions sufficient to form NACA.

In one aspect of the above embodiment, the alcohol is selected from the group consisting of methanol, ethanol, propanol, iso-propanol and butanol. In another aspect, the alcohol is methanol. In another aspect of the process, the acid is selected from the group consisting of sulfuric acid, hydrochloric acid and phosphoric acid or a combination thereof. In one particular aspect, the acid is sulfuric acid.

In another embodiment of the above process, the base is selected from the group consisting of sodium bicarbonate, sodium hydrogen carbonate, potassium bicarbonate, potassium hydrogen carbonate, lithium carbonate or a combination thereof. In one particular aspect, the base is sodium bicarbonate.

In another aspect of any of the above embodiments and aspects, the step c) further comprises adding an organic solvent to the neutralized mixture. In another aspect, the organic solvent is selected from the group consisting of ethyl acetate, tetrahydrofuran, methylethylketone and dichloromethane. In one aspect, the organic solvent is ethyl acetate.

In yet another aspect of the above process, the step c) comprises drying the organic solution with a drying agent. In one aspect of the above, the drying agent is anhydrous sodium sulfate. In yet another aspect of the process, the ammonia is aqueous ammonium hydroxide.

In another aspect of any of the above embodiments and aspects, the step of contacting of the N-acetyl-L-cysteine ester with ammonia is performed at room temperature. In another aspect, the step d) of removing the organics under reduced pressure is performed at about 45° C. In one variation, removal of the organics may be performed at about 45° C. or less, 40° C. or less or 35° C. or less. In another aspect of the process, the separated organic solution in step c) is further filtered to remove solids.

In another aspect of the above embodiments and aspects, the process provides NACA in about 70% yield, about 75% yield, about 85% yield or about 95% yield or more. In another aspect, the process provides NACA in greater than 90% enatiomeric excess (e.e.), 95% e.e, 97% e.e., 98% e.e., or greater than 99% e.e. as determined by optical rotation in methanol.

In one aspect of the process, the alcohol is selected from the group consisting of methanol, ethanol, propanol, iso-propanol and butanol. In another aspect, the alcohol is methanol.

In another aspect of the process, the acid is selected from the group consisting of sulfuric acid, hydrochloric acid and phosphoric acid or a combination thereof. In another aspect, the acid is sulfuric acid. In another aspect, the base is selected from the group consisting of sodium bicarbonate, sodium hydrogen carbonate, potassium bicarbonate, potassium hydrogen carbonate, lithium carbonate or a combination thereof. In another aspect, the base is sodium bicarbonate.

In another aspect of the process, in step c), the process further comprising adding an organic solvent to the neutralized mixture. In another aspect, the organic solvent is selected from the group consisting of ethyl acetate, tetrahydrofuran, methylethylketone and dichloromethane. In one particular aspect, the organic solvent is ethyl acetate.

In yet another aspect of the process, in step c), the process comprises drying the organic solution with a drying agent. In another aspect, the drying agent is anhydrous sodium sulfate. In yet another aspect, the ammonia is aqueous ammonium hydroxide.

In another aspect of the process, the contacting of the N-acetyl-L-cysteine ester with ammonia is performed at room temperature. In another aspect of the process, the step d) of removing the organics under reduced pressure is performed at about 45° C. In one variation, removal of the organics may be performed at about 45° C. or less, 40° C. or less or 35° C. or less. In another aspect of the process, the separated organic solution in step c) is further filtered to remove solids. In yet another aspect, the process provides NACA in about 70% yield or greater.

DETAILED DESCRIPTION OF THE APPLICATION

Experiments

The following procedures may be employed for the preparation of the compound of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

Preparation of N-Acetyl Cysteine Amide (NACA)

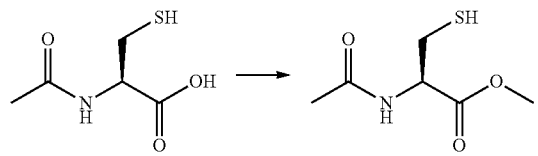

N-Acetyl Cysteine Methyl Ester:

A suspension of N-acetyl-L-cysteine (32.6 g) in dry methanol (120 mL) under nitrogen was stirred for 15 minutes and treated dropwise with concentrated sulfuric acid (0.8 mL) at room temperature with vigorous stirring. After 22 hours of stirring, the mixture was treated with water (25 mL) and the volatiles were removed under reduced pressure. The resulting residue was diluted with ethyl acetate (200 mL), washed with aqueous saturated sodium bicarbonate (150 mL) and the layers were allowed to separate.

The organic layer was separated from the aqueous layer and dried over anhydrous sodium sulfate. The aqueous layer was re-extracted with ethyl acetate (2×100 mL). The combined organic extract was filtered and concentrated in vacuo to yield N-Acetyl-L-cysteine methyl ester (24.1 g, 68%) as a white crystalline solid: $^1$H NMR (400 MHz DMSO-$d_6$) δ (ppm): 8.29 (d, 1H), 4.39 (m, 1H), 3.60 (s, 3H), 2.77 (dd, 1H), 2.70 (dd, 1H), 2.51 (s, 1H), 1.84 (s, 3H); LRMS: 178.13 $(M+H)^+$.

Scale-up Preparation of N-Acetyl Cysteine Methyl Ester:

To a suspension of N-acetyl-L-cysteine (162.7 g) in dry methanol (600 mL) under nitrogen was added concentrated $H_2SO_4$ (4 mL) drop-wise at room temperature with vigorous stirring. After 24 hours of stirring, the mixture was slowly treated with saturated aqueous sodium bicarbonate solution (100 mL) and stirred for 1 hour.

The solvent was removed under reduced pressure, and the resulting aqueous portion was extracted with dichloromethane (4×100 mL), dried over anhydrous sodium sulfate, concentrated and vacuum-dried to afford the desired methyl ester product as an off-white solid (120 g).

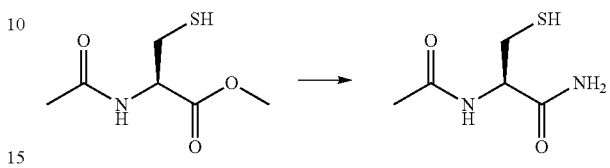

N-Acetyl-L-Cysteine Amide (NACA):

N-Acetyl-L-cysteine methyl ester (10 g) under a flush of nitrogen was treated with ammonium hydroxide (28% aqueous, 66 mL) over 10 minutes at room temperature and stirred for 6 hours. The resulting solution was concentrated in vacuo and ethanol (100 mL) was added. The resulting solution was concentrated again under reduced pressure at 48° C., then subjected to high vacuum overnight to afford N-acetyl-L-cysteine amide (NACA, 9.12 g) as a white crystalline solid (m.p. 138-141° C.; Lit. 148-150° C.); $^1$H NMR (400 MHz DMSO-$d_6$) δ (ppm): 7.89 (d, 1H), 7.30 (s, 1H), 7.01 (s, 1H), 4.16 (m, 1H), 2.64 (dd, 1H), 2.52 (dd, 1H), 1.74 (s, 3H); LRMS 163.13 $(M+H)^+$.

Alternative preparation of NACA. To N-Acetyl cysteine methyl ester (120 g, 0.67 mol) under nitrogen was added ammonium hydroxide solution (750 mL) at room temperature. After stirring at room temperature under N2 atmosphere for 24 hours, the excess ammonia was removed under reduced pressure. The rest of the reaction solution was azeotroped with ethanol (600 mL) at 48° C. under reduced pressure leaving a solid product which was dried under high vacuum overnight.

The solid was recrystallized from hot ethanol to give an off-white solid (102 g) m.p. 139-143° C. The $^1$NMR showed primarily the desired product together with ~4-5% of disulfide of N-acetyl-L-cysteine amide (di-NACA) as impurity. The crude solid was further purified on combi-flash silica gel column using 1-10% methanol-dichloromethane gradient to afford high-grade NACA product (62 g) as a colorless crystalline solid; (m.p. 147-151° C.; Lit. m.p. 148-150° C.).

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope. The entire disclosures of all documents cited throughout this application are incorporated herein by reference.

What is claimed is:

1. A process comprising:
    contacting N-acetyl-L-cysteine with an organic alcohol and an inorganic acid to form an organic solution containing N-acetyl-L-cysteine ester;
    neutralizing the acid in the organic solution with an aqueous solution containing a base to form a neutralized mixture;
    separating an organic solution containing N-acetyl-L-cysteine ester from the neutralized mixture;

removing the N-acetyl-L-cysteine ester from the organic solution under reduced pressure; and contacting the N-acetyl-L-cysteine ester with ammonia.

2. The process of claim 1, wherein the organic alcohol is an alkyl alcohol.

3. The process of claim 2, wherein the alkyl alcohol is methanol, ethanol, propanol, iso-propanol or butanol.

4. The process of claim 2, wherein the alcohol is methanol.

5. The process of claim 1, wherein the inorganic acid is sulfuric acid, hydrochloric acid, phosphoric acid, or a combination thereof.

6. The process of claim 5, wherein the acid is sulfuric acid.

7. The process of claim 1, wherein the base is sodium bicarbonate, sodium hydrogen carbonate, potassium bicarbonate, potassium hydrogen carbonate, lithium carbonate or a combination thereof.

8. The process of claim 6, wherein the base is sodium bicarbonate.

9. The process of claim 1, wherein step c), further comprises adding an organic solvent to the neutralized mixture.

10. The process of claim 9, wherein the organic solvent is ethyl acetate, tetrahydrofuran, methylethylketone or dichloromethane.

11. The process of claim 9, wherein the organic solvent is ethyl acetate.

12. The process of claim 1, further comprising drying the organic solution removed from the neutralized mixture with a drying agent.

13. The process of claim 12, wherein the drying agent is anhydrous sodium sulfate.

14. The process of claim 1, wherein the ammonia is provide in the form of aqueous ammonium hydroxide.

15. The process of claim 1, wherein the contacting of the N-acetyl-L-cysteine ester with ammonia is performed at room temperature.

16. The process of claim 1, wherein the removing the organics under reduced pressure is performed at about 45° C. or less.

17. The process of claim 1, wherein the removing the organics under reduced pressure is performed at about 35° C. or less.

18. The process of claim 1, wherein the removing the organics under reduced pressure is performed at about 30° C. or less.

19. The process of claim 1, wherein the removing the organics under reduced pressure is performed at about 45° C.

20. The process of claim 1, wherein the organic solution removed from the neutralized mixture is filtered to remove solids.

* * * * *